United States Patent
Yin et al.

(10) Patent No.: US 12,190,473 B2
(45) Date of Patent: Jan. 7, 2025

(54) SUPER-RESOLUTION FLOW FIELD RECONSTRUCTION METHOD AND DEVICE THEREOF

(71) Applicant: Nanjing Leapsonics Technology Co., Ltd., Nanjing (CN)

(72) Inventors: Jingyi Yin, Nanjing (CN); Jiabin Zhang, Nanjing (CN); Jue Zhang, Nanjing (CN)

(73) Assignee: Nanjing Leapsonics Technology Co., Ltd., Nanjing (CN)

( * ) Notice: Subject to any disclaimer, the term of this patent is extended or adjusted under 35 U.S.C. 154(b) by 384 days.

(21) Appl. No.: 17/720,707

(22) Filed: Apr. 14, 2022

(65) Prior Publication Data
US 2022/0245763 A1    Aug. 4, 2022

Related U.S. Application Data

(63) Continuation of application No. PCT/CN2021/077028, filed on Feb. 20, 2021.

(30) Foreign Application Priority Data

May 18, 2020  (CN) .......................... 202010419628.0

(51) Int. Cl.
*G06T 3/4053*    (2024.01)
*A61B 8/08*    (2006.01)
(Continued)

(52) U.S. Cl.
CPC ............ *G06T 3/4053* (2013.01); *A61B 8/481* (2013.01); *A61B 8/5246* (2013.01); *G06T 5/50* (2013.01);
(Continued)

(58) Field of Classification Search
CPC ......... A61B 8/06; A61B 8/481; A61B 8/5246; G06T 2207/10132; G06T 2207/20221;
(Continued)

(56) References Cited

U.S. PATENT DOCUMENTS

| 2001/0001108 A1* | 5/2001 | Lizzi | ........................ A61B 8/06 |
| | | | 600/458 |
| 2008/0015440 A1* | 1/2008 | Shandas | .................... A61B 8/13 |
| | | | 600/458 |

(Continued)

FOREIGN PATENT DOCUMENTS

| CN | 1658798 A | 8/2005 |
| CN | 107361791 A | 11/2017 |

(Continued)

OTHER PUBLICATIONS

Oren Solomon et al., "Exploiting Flow Dynamics for Superresolution in Contrast-Enhanced Ultrasound," Sep. 25, 2019, IEEE Transactions on Ultrasonics, Ferroelectrics, and Frequency Control, vol. 66, No. 10, Oct. 2019, pp. 1573-1584.*

(Continued)

*Primary Examiner* — Omar S Ismail
(74) *Attorney, Agent, or Firm* — Westbridge IP LLC

(57) ABSTRACT

Disclosed is a super-resolution flow field reconstruction method, including: superimposing a plurality of frames of contrast-enhanced ultrasound images that are in one time interval and each of which includes images of a plurality of microbubbles, to obtain a superimposed image including a plurality of microbubble trajectories of the plurality of microbubbles; performing straight line fitting on the plurality of microbubble trajectories, to obtain a plurality of microbubble trajectory straight lines of the plurality of microbubbles, respectively; determining directions and velocities of instantaneous movements of the plurality of microbubbles in the time interval; and reconstructing a
(Continued)

Superimposing a plurality of frames of contrast-enhanced ultrasound images that are in one time interval and each of which includes images of a plurality of microbubbles, to obtain a superimposed image including a plurality of microbubble trajectories of the plurality of microbubbles — 101

Performing straight line fitting on the plurality of microbubble trajectories, to obtain a plurality of angiography trajectory straight lines of the plurality of microbubbles, respectively — 102

Determining, based on directions and lengths of the plurality of microbubble trajectory straight lines of the plurality of microbubbles and a quantity of superimposed frames and a frame rate of the plurality of frames of contrast-enhanced ultrasound images, directions and velocities of instantaneous movements of the plurality of microbubbles in the time interval — 103

Reconstructing a super-resolution flow field based on directions and velocities of instantaneous movements of the plurality of microbubbles in each of different time intervals — 104 super-resolution flow field. This method avoids localization and tracking process of the plurality of moving microbubbles, overcomes the limitations of current ultrasound super-resolution imaging strategies under the impact of motion artifacts and low signal-to-noise-ratio, and improving precision and efficiency of super-resolution flow field reconstruction.

18 Claims, 9 Drawing Sheets

(51) Int. Cl.
G06T 5/50 (2006.01)
G06T 5/92 (2024.01)
G06T 7/00 (2017.01)
G06T 7/30 (2017.01)
G06T 7/60 (2017.01)
G06T 7/70 (2017.01)

(52) U.S. Cl.
CPC .......... *G06T 5/92* (2024.01); *G06T 7/0012* (2013.01); *G06T 7/30* (2017.01); *G06T 7/60* (2013.01); *G06T 7/70* (2017.01); *G06T 2207/10132* (2013.01); *G06T 2207/20221* (2013.01); *G06T 2207/30104* (2013.01); *G06T 2207/30241* (2013.01)

(58) Field of Classification Search
CPC . G06T 2207/30104; G06T 2207/30241; G06T 3/18; G06T 3/4053; G06T 5/50; G06T 5/92; G06T 7/0012; G06T 7/246; G06T 7/30; G06T 7/60; G06T 7/70
See application file for complete search history.

(56) References Cited

U.S. PATENT DOCUMENTS

| | | | | |
|---|---|---|---|---|
| 2014/0147013 | A1* | 5/2014 | Shandas | G06T 7/0016 382/107 |
| 2019/0129026 | A1* | 5/2019 | Sumi | A61B 6/00 |
| 2019/0154822 | A1* | 5/2019 | Berlin | A61B 8/06 |
| 2019/0196013 | A1* | 6/2019 | Stanziola | G01S 15/8927 |
| 2019/0216436 | A1* | 7/2019 | Miyazawa | A61B 8/54 |
| 2019/0223841 | A1* | 7/2019 | Miyazawa | A61B 8/565 |
| 2020/0064468 | A1* | 2/2020 | Holbek | G01S 15/8993 |
| 2020/0305840 | A1* | 10/2020 | Sboros | G06T 7/73 |
| 2021/0374910 | A1* | 12/2021 | Song | G01S 15/89 |

FOREIGN PATENT DOCUMENTS

| | | |
|---|---|---|
| CN | 107753062 A | 3/2018 |
| CN | 109803588 A | 5/2019 |
| CN | 110740688 A | 1/2020 |
| CN | 111598782 A | 8/2020 |
| WO | 2020081915 A1 | 4/2020 |

OTHER PUBLICATIONS

P. L. van Gent et al., "Comparative assessment of pressure field reconstructions from particle image velocimetry measurements and Lagrangian particle tracking," Mar. 27, 2017, Exp Fluids (2017) 58:33, pp. 2-15.*
Douglas Barker et al., "A parallel algorithm for 3D particle tracking and Lagrangian trajectory reconstruction," Dec. 16, 2011, Meas. Sci. Technol. 23 (2012) 025301, pp. 3-12.*
Kirsten Christensen-Jeffries et al., "Microbubble Axial Localization Errors in Ultrasound Super-Resolution Imaging," Oct. 24, 2017, IEEE Transactions on Ultrasonics, Ferroelectrics, and Frequency Control, vol. 64, No. 11, Nov. 2017, pp. 1644-1651.*
Chee Hau Leow et al., "Spatio-Temporal Flow Andwall Shear Stress Mapping Based on Incoherent Ensemble-Correlation of Ultrafast Contrast Enhanced Ultrasound Images," Aug. 14, 2017, Ultrasound in Med. & Biol., vol. 44, No. 1, pp. 134-149.*
Dimitri Ackermann et al., "Detection and Tracking of Multiple Microbubbles in Ultrasound B-Mode Images," Dec. 29, 2015, IEEE Transactions on Ultrasonics, Ferroelectrics, and Frequency Control, vol. 63, No. 1, Jan. 2016, pp. 72-79.*
First Office Action issued in counterpart Chinese Patent Application No. 202010419628.0, dated Jun. 2, 2021.
International Search Report issued in corresponding PCT Application No. PCT/CN2021/077028, dated May 21, 2021.
Second Office Action issued in counterpart Chinese Patent Application No. 202010419628.0, dated Feb. 21, 2022.
Wu et al., Image Processing Algorithm for Particle Trajectory Image and Reconstruction Study on Flow Field, Journal of Experiments in Fluid Mechanics, vol. 33, No. 4, pp. 100-107, dated Aug. 31, 2019.

* cited by examiner

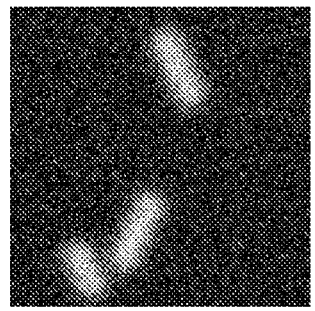

FIG. 4B

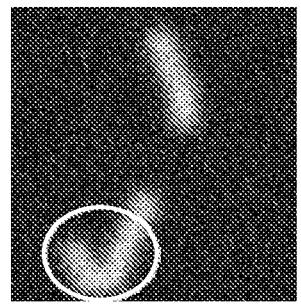

FIG. 4C

| Performing registration on the plurality of frames of contrast-enhanced ultrasound images that are in the one time interval and each of which includes the images of the plurality of microbubbles, to obtain a plurality of frames of registered contrast-enhanced ultrasound images each including the images of the plurality of microbubbles | 501 |

↓

| Superimposing the plurality of frames of registered contrast-enhanced ultrasound images that are in the one time interval and each of which includes the images of the plurality of microbubbles, to obtain the superimposed image including the plurality of microbubble trajectories of the plurality of microbubbles | 502 |

FIG. 5

| Superimposing the plurality of frames of contrast-enhanced ultrasound images that are in the one time interval and each of which includes the images of the plurality of microbubbles, to obtain a superimposed image including a plurality of preliminary microbubble trajectories of the plurality of microbubbles | 601 |

↓

| Separately performing skeleton extraction on the plurality of preliminary microbubble trajectories in the superimposed image, to obtain the plurality of microbubble trajectories | 602 |

FIG. 6

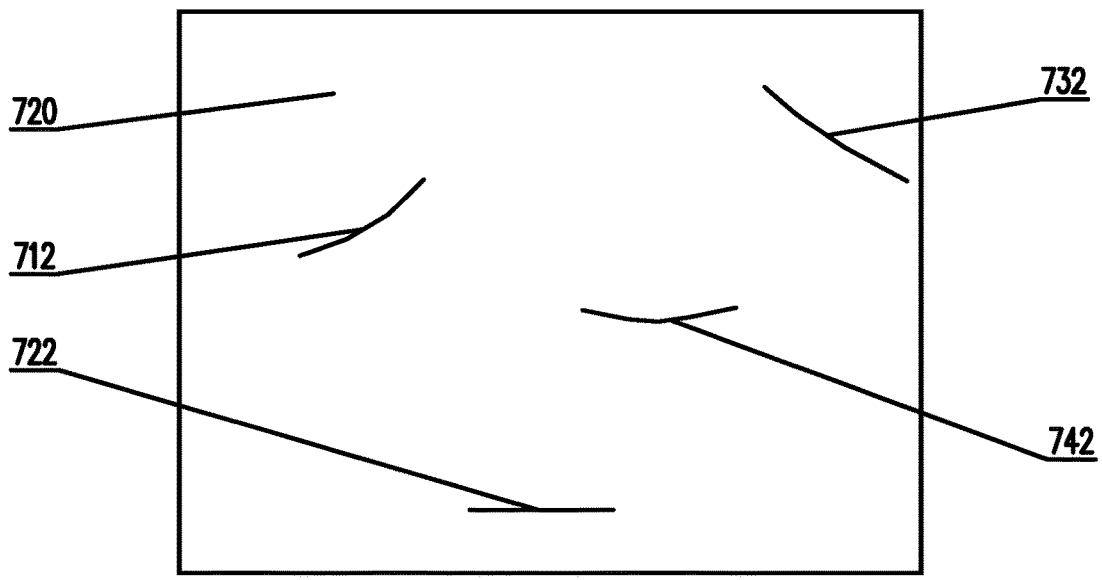

FIG. 7C

| Determining, based on the directions and velocities of instantaneous movements of the plurality of microbubbles in each of the different time intervals, directions and velocities of instantaneous movements of the plurality of microbubbles, in each of the different time intervals, corresponding to a plurality of pixel coordinates | — 801 |
|---|---|
| Reconstructing the super-resolution flow field based on the directions and velocities of instantaneous movements of the plurality of microbubbles, in each of the different time intervals, corresponding to the plurality of pixel coordinates | — 802 |

FIG. 8

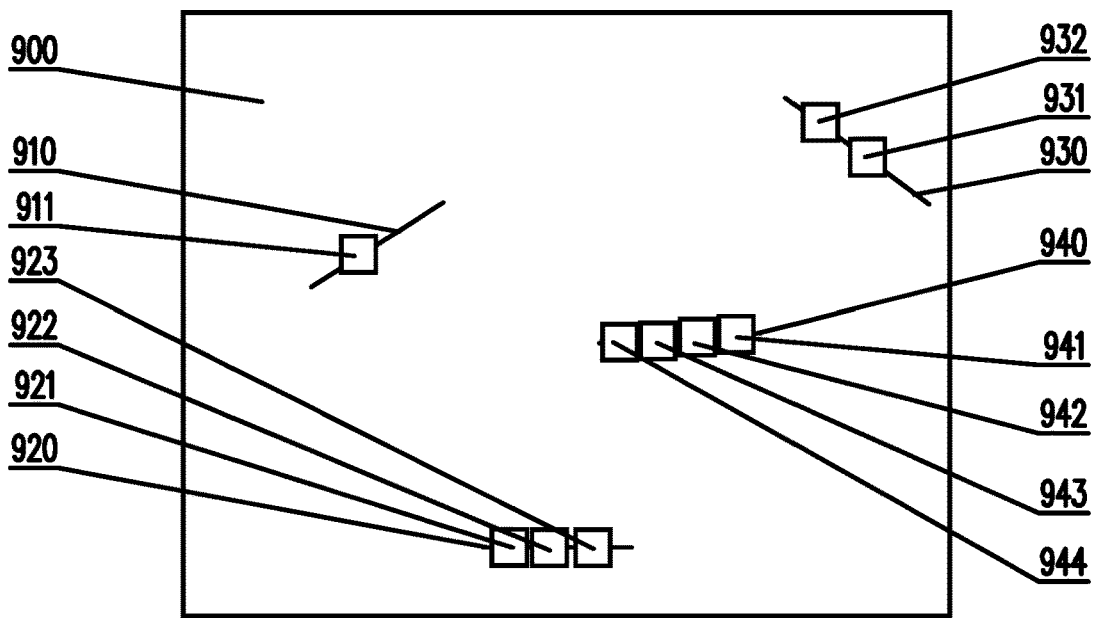

FIG. 9

SUPER-RESOLUTION FLOW FIELD RECONSTRUCTION METHOD AND DEVICE THEREOF

CROSS-REFERENCE TO RELATED APPLICATIONS

This application is a continuation of International Application No. PCT/CN2021/077028, filed on Feb. 20, 2021, which claims priority to Chinese Patent Application No. 202010419628.0, filed on May 18, 2020. The entire contents of both applications are incorporated herein by reference in their entireties.

TECHNICAL FIELD

The present application relates to the field of ultrasound imaging technologies, and in particular, to a super-resolution flow field reconstruction method, an electronic device, and a computer-readable storage medium.

BACKGROUND

Functional parameters such as a blood flow velocity and a blood flow direction are of great significance in disease diagnosis. An ultrasound Doppler technique is widely used in clinical blood flow functional imaging due to its safety, non-invasiveness and low cost, but the spatial resolution of a conventional Doppler technique is limited by diffraction limit. On the basis of microbubble perfusion and contrast-enhanced ultrasound imaging, by combining sparse microbubble localization, accumulation, and the nearest neighbor tracking strategy, the super-resolution image of blood flow velocity and flow direction is reconstructed, which breaks the acoustic diffraction limit. However, the signal-to-noise-ratio and contrast-to-noise-ratio of microbubble signals may be easily affected by inevitable motion artifacts and noise, especially during in vivo human imaging. Therefore, conventional ultrasound super-resolution imaging methods based on microbubble localization are prone to generate false localizations, resulting in a relatively large match error during subsequent nearest-neighbor tracking.

SUMMARY

In view of this, embodiments of the present application provide a super-resolution flow field reconstruction method, an electronic device, and a computer-readable storage medium, overcoming the limitations of current ultrasound super-resolution imaging strategies during microbubble localization and tracking process under the impact of motion artifacts and low signal-to-noise-ratio, and improving precision and efficiency of super-resolution flow field reconstruction.

According to an aspect of the present application, a super-resolution flow field reconstruction method is provided, including: superimposing a plurality of frames of contrast-enhanced ultrasound images that are in one time interval and each of which includes images of a plurality of microbubbles, to obtain a superimposed image including a plurality of microbubble trajectories of the plurality of microbubbles; performing straight line fitting on the plurality of microbubble trajectories, to obtain a plurality of microbubble trajectory straight lines of the plurality of microbubbles, respectively; determining, based on directions and lengths of the plurality of microbubble trajectory straight lines of the plurality of microbubbles and a quantity of superimposed frames and a frame rate of the plurality of frames of contrast-enhanced ultrasound images, directions and velocities of instantaneous movements of the plurality of microbubbles are calculated in the time interval; and reconstructing a super-resolution flow field based on directions and velocities of instantaneous movements of the plurality of microbubbles in each of different time intervals.

In an embodiment, the superimposing a plurality of frames of contrast-enhanced ultrasound images that are in one time interval and each of which includes images of a plurality of microbubbles, to obtain a superimposed image including a plurality of microbubble trajectories of the plurality of microbubbles includes: performing registration on the plurality of frames of contrast-enhanced ultrasound images that are in the one time interval and each of which includes the images of the plurality of microbubbles, to obtain a plurality of frames of registered contrast-enhanced ultrasound images each including the images of the plurality of microbubbles; and superimposing the plurality of frames of registered contrast-enhanced ultrasound images that are in the one time interval and each of which includes the images of the plurality of microbubbles, to obtain the superimposed image including the plurality of microbubble trajectories of the plurality of microbubbles.

In an embodiment, the performing registration on the plurality of frames of contrast-enhanced ultrasound images that are in the one time interval and each of which includes the images of the plurality of microbubbles, to obtain a plurality of frames of registered contrast-enhanced ultrasound images each including the images of the plurality of microbubbles includes: performing, by using a multi-scale registration method, registration on the plurality of frames of contrast-enhanced ultrasound images that are in the one time interval and each of which includes the images of the plurality of microbubbles, to obtain the plurality of frames of registered contrast-enhanced ultrasound images each including the images of the plurality of microbubbles.

In an embodiment, the multi-scale registration method includes global decomposition, local decomposition, and detail decomposition according to decomposition scale.

In an embodiment, the superimposing a plurality of frames of contrast-enhanced ultrasound images that are in one time interval and each of which includes images of a plurality of microbubbles, to obtain a superimposed image including a plurality of microbubble trajectories of the plurality of microbubbles includes: superimposing a plurality of consecutive frames of contrast-enhanced ultrasound images that are in the one time interval and each of which includes the images of the plurality of microbubbles, to obtain the superimposed image including the plurality of microbubble trajectories of the plurality of microbubbles.

In an embodiment, the superimposing a plurality of consecutive frames of contrast-enhanced ultrasound images that are in the one time interval and each of which includes the images of the plurality of microbubbles, to obtain the superimposed image including the plurality of microbubble trajectories of the plurality of microbubbles includes: superimposing two, three, or four consecutive frames of contrast-enhanced ultrasound images that are in the one time interval and each of which includes the images of the plurality of microbubbles, to obtain the superimposed image including the plurality of microbubble trajectories of the plurality of microbubbles.

In an embodiment, the different time intervals include: different time intervals that include a same quantity of frames and whose start frames have a same interval.

In an embodiment, the superimposing a plurality of frames of contrast-enhanced ultrasound images that are in one time interval and each of which includes images of a plurality of microbubbles, to obtain a superimposed image including a plurality of microbubble trajectories of the plurality of microbubbles includes: superimposing the plurality of frames of contrast-enhanced ultrasound images that are in the one time interval and each of which includes the images of the plurality of microbubbles, to obtain a superimposed image including a plurality of preliminary microbubble trajectories of the plurality of microbubbles; and separately performing skeleton extraction on the plurality of preliminary microbubble trajectories in the superimposed image of the plurality of preliminary microbubble trajectories of the plurality of microbubbles, to obtain the plurality of microbubble trajectories.

In an embodiment, the separately performing skeleton extraction on the plurality of preliminary microbubble trajectories in the superimposed image of the plurality of preliminary microbubble trajectories of the plurality of microbubbles includes: separately performing, by using an iterative erosion algorithm, the skeleton extraction on the plurality of preliminary microbubble trajectories in the superimposed image.

In an embodiment, the separately performing skeleton extraction on the plurality of preliminary microbubble trajectories in the superimposed image of the plurality of preliminary microbubble trajectories of the plurality of microbubbles includes: separately performing, by using a circumscribed rectangle-maximum grayscale integral axis extraction algorithm, the skeleton extraction on the plurality of preliminary microbubble trajectories in the superimposed image.

In an embodiment, the determining, based on directions and lengths of the plurality of microbubble trajectory straight lines of the plurality of microbubbles and a quantity of superimposed frames and a frame rate of the plurality of frames of contrast-enhanced ultrasound images, directions and velocities of instantaneous movements of the plurality of microbubbles in the time interval includes: determining, based on the directions of the plurality of microbubble trajectory straight lines of the plurality of microbubbles, the directions of instantaneous movements of the plurality of microbubbles in the time interval; and determining, based on a product of the frame rate and a ratio of the lengths of the microbubble trajectory straight lines of the plurality of microbubbles to the quantity of superimposed frames of the plurality of frames of contrast-enhanced ultrasound images, the velocities of instantaneous movements of the plurality of microbubbles in the time interval.

In an embodiment, each microbubble trajectory straight line of each microbubble in the plurality of microbubble trajectory straight lines of the plurality of microbubbles includes at least one pixel coordinate; and the reconstructing a super-resolution flow field based on directions and velocities of instantaneous movements of the plurality of microbubbles in each of different time intervals includes: determining, based on the directions and velocities of instantaneous movements of the plurality of microbubbles in each of the different time intervals, directions and velocities of instantaneous movements of the plurality of microbubbles, in each of the different time intervals, corresponding to a plurality of pixel coordinates; and reconstructing the super-resolution flow field based on the directions and velocities of instantaneous movements of the plurality of microbubbles, in each of the different time intervals, corresponding to the plurality of pixel coordinates.

In an embodiment, a plurality of microbubble trajectories of the each microbubble include same pixel coordinates, and the reconstructing the super-resolution flow field includes: calculating a frequency of occurrence of each of directions and velocities of instantaneous movements corresponding to the same pixel coordinates of the each microbubble, and selecting a direction and a velocity with the highest frequency of occurrence at every pixel coordinate to reconstruct the super-resolution flow field.

In an embodiment, a plurality of microbubble trajectories of the each microbubble include same pixel coordinates, and reconstructing the super-resolution flow field includes: calculating an average value of directions and velocities of instantaneous movements corresponding to the same pixel coordinates of the each microbubble, to reconstruct the super-resolution flow field.

In an embodiment, a plurality of microbubble trajectories of the each microbubble include same pixel coordinates, and the reconstructing the super-resolution flow field includes: calculating a maximum value of directions and velocities of instantaneous movements corresponding to the same pixel coordinates of the each microbubble to reconstruct the super-resolution flow field.

In an embodiment, the performing straight line fitting on the plurality of microbubble trajectories, to obtain a plurality of microbubble trajectory straight lines of the plurality of microbubbles, respectively includes: performing, by using the Hough transform-based straight line detection method on the plurality of microbubble trajectories, to obtain the plurality of microbubble trajectory straight lines of the plurality of microbubbles, respectively.

According to another aspect of the present application, an electronic device is provided, including: a processor; and a memory. The memory stores computer program instructions, and when the computer program instructions are run by the processor, the processor is enabled to perform the super-resolution flow field reconstruction method according to any one of the foregoing embodiments.

In an embodiment, when the computer program instructions are run by the processor, the processor is enabled to: perform registration on the plurality of frames of contrast-enhanced ultrasound images that are in the one time interval and each of which comprises the images of the plurality of microbubbles, to obtain a plurality of frames of registered contrast-enhanced ultrasound images each comprising the images of the plurality of microbubbles; and superimpose the plurality of frames of registered contrast-enhanced ultrasound images that are in the one time interval and each of which comprises the images of the plurality of microbubbles, to obtain the superimposed image comprising the plurality of contrast-enhanced ultrasound images of the plurality of microbubbles.

In an embodiment, when the computer program instructions are run by the processor, the processor is enabled to: superimpose a plurality of consecutive frames of contrast-enhanced ultrasound images that are in the one time interval and each of which comprises the images of the plurality of microbubbles, to obtain the superimposed image comprising the plurality of microbubble trajectories of the plurality of microbubbles.

According to another aspect of the present application, a computer-readable storage medium is provided. The computer-readable storage medium stores computer program instructions for executing the super-resolution flow field reconstruction method according to any one of the foregoing embodiments.

According to the super-resolution flow field reconstruction method, the electronic device, and the computer-readable storage medium provided in the embodiments of the present application, parameters of instantaneous movements of the plurality of microbubbles in the one time interval are calculated by utilizing trajectories formed in the plurality of frames of superimposed contrast-enhanced ultrasound images of the plurality of microbubbles in the one time interval, and the super-resolution flow field is then reconstructed based on parameters of instantaneous movements of the plurality of microbubbles in each of the different time intervals, which avoids localization and tracking process of the plurality of moving microbubbles, overcoming the limitations of current ultrasound super-resolution imaging strategies under the impact of motion artifacts and low signal-to-noise-ratio, and improves precision and efficiency of super-resolution flow field reconstruction.

BRIEF DESCRIPTION OF DRAWINGS

FIG. 4B shows a superimposed image of three consecutive frames of contrast-enhanced ultrasound images according to another embodiment of the present application.

FIG. 4C shows a superimposed image of four consecutive frames of contrast-enhanced ultrasound images according to another embodiment of the present application.

FIG. 5 is a schematic flowchart diagram of a super-resolution flow field reconstruction method according to another embodiment of the present application.

FIG. 6 is a schematic flowchart diagram of a super-resolution flow field reconstruction method according to another embodiment of the present application.

FIG. 7C is a schematic diagram of a superimposed image including a plurality of microbubble trajectories according to another embodiment of the present application.

FIG. 8 is a schematic flowchart diagram of a super-resolution flow field reconstruction method according to another embodiment of the present application.

FIG. 9 is a schematic diagram of an image including a plurality of microbubble trajectory straight lines of a plurality of microbubbles according to another embodiment of the present application.

DETAILED DESCRIPTION OF THE EMBODIMENTS

Figure 1:
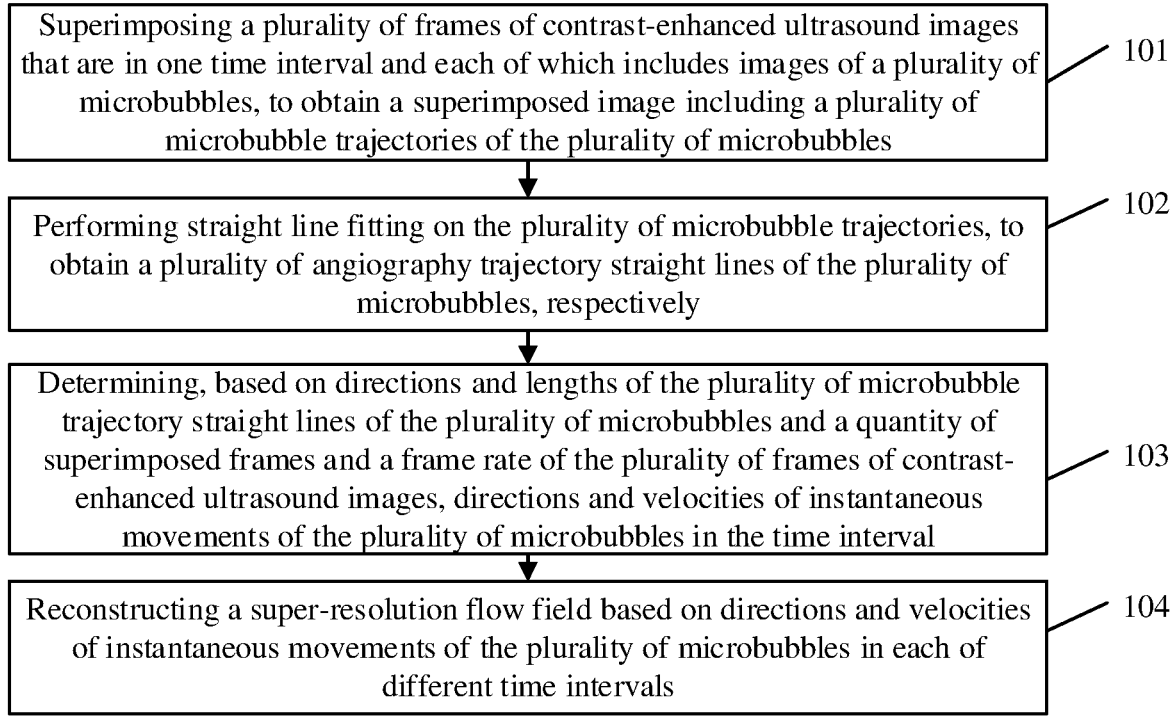
FIG. 1 is a schematic flowchart diagram of a super-resolution flow field reconstruction method according to an embodiment of the present application.

The technical schemes in the embodiments of the present disclosure will be described clearly and completely below in combination with the accompanying drawings in the embodiments of the present disclosure. Obviously, the described embodiments are only a part of the embodiments of the present disclosure, not all of the embodiments. Based on the embodiments in the present disclosure, all other embodiments obtained by those skilled in the art without creative efforts shall fall within the protection scope of the present disclosure.

Overview

As mentioned above, the existing super-resolution flow field reconstruction method has problems of low precision and low efficiency during clinical application mainly due to the fact that accurate localization and tracking need to be performed and guaranteed on moving microbubbles. However, the signal-to-noise-ratio and contrast-to-noise-ratio of microbubble signals can be easily affected by inevitable artifacts and noise induced by physiologic and operator-induced motion, causing unreliable microbubble localization, accumulation, and tracking. Therefore, conventional ultrasound super-resolution imaging methods based on microbubble localization are prone to generate false localizations, resulting in a relatively large match error during subsequent nearest-neighbor tracking.

For the foregoing technical problems, a basic idea of the present application is to provide a super-resolution flow field reconstruction method, which may avoid localization and tracking process of moving microbubbles, and only requires the acquisition of a plurality of frames of contrast-enhanced ultrasound images including images of the microbubble and the process the plurality of frames of contrast-enhanced ultrasound images including the images of the microbubble, to obtain movement velocities and movement directions of microbubbles. Since the microbubble flows along a track of a flow field, a movement velocity and a movement direction of the microbubble are a flow velocity and a flow direction of the flow field, respectively. For example, when the microbubble flows in a blood vessel, a movement velocity and a movement direction of the microbubble are a flow velocity and a flow direction of blood, respectively. Therefore, when the movement velocities and the movement directions of microbubbles are obtained, the flow velocities and directions of the flow field are obtained, thereby implementing reconstruction of a super-resolution flow field. Flow field reconstruction is implemented by utilizing a plurality of frames of contrast-enhanced ultrasound images including images of microbubbles, which avoids localization and tracking of moving microbubbles, overcomes the limitations of current ultrasound super-resolution imaging strategies under the impact of motion artifacts and low signal-to-noise-ratio, and improves precision and efficiency of super-resolution flow field reconstruction.

The super-resolution flow field reconstruction method and device provided in the present application may be applied to any application scenario where super-resolution flow field reconstruction is applicable. For example, in a diagnostic process of cardiovascular diseases, contrast-enhanced ultrasound imaging and super-resolution flow field reconstruction are performed to evaluate the blood flow around the heart, in order to assist doctors to better analyze the physiological structures of blood vessels physiological parameters related to the blood flow around the heart. In a cancer diagnostic process, contrast-enhanced ultrasound imaging and super-resolution flow field reconstruction are performed on blood flow in the tumor, to assist doctors to better analyze physiological structures and physiological parameters of blood vessels related to the tumor, and the like. An application scenario where the super-resolution flow field reconstruction is applicable is not specifically limited in the present application.

After the basic principle of the present application is introduced, the following describes various non-limiting embodiments of the present application in detail with reference to the accompanying drawings.

Exemplary Super-Resolution Flow Field Reconstruction Methods

FIG. 1 is a schematic flowchart diagram of a super-resolution flow field reconstruction method according to an embodiment of the present application. As shown in FIG. 1, the super-resolution flow field reconstruction method includes the following steps.

Step 101: superimposing a plurality of frames of contrast-enhanced ultrasound images that are in one time interval and each of which includes images of a plurality of microbubbles, to obtain a superimposed image including a plurality of microbubble trajectories of the plurality of microbubbles.

Specifically, the contrast-enhanced ultrasound image may be an image shot by utilizing an ultrasound imaging system after an ultrasound contrast agent is injected into blood. The ultrasound contrast agent is a liquid containing microbubbles with diameters of a few microns. After the ultrasound contrast agent is injected into the blood, microbubble contrast agents may vibrate in an ultrasound field and then scatter strong ultrasonic signals, thereby displaying microbubble images on the image.

The image of the microbubble in the contrast-enhanced ultrasound image may be a point spread function image in which the microbubble is diffused a specific radius by taking the microbubble as the center. Due to a diffraction of ultrasonic waves emitted from the ultrasound imaging system, the image of the microbubble presented in the contrast-enhanced ultrasound image is an image in which the microbubble may be approximated by a two-dimensional Gaussian distribution, namely, a point spread function image of the microbubble.

In each frame of contrast-enhanced ultrasound images, each microbubble has a corresponding point spread function image. After the plurality of frames of contrast-enhanced ultrasound images including the images of the plurality of microbubbles are superimposed, the point spread function images of each microbubble in the plurality of frames of contrast-enhanced ultrasound images may partially overlap. Therefore, in the superimposed image, one microbubble trajectory may be obtained for each microbubble.

Figure 2A:
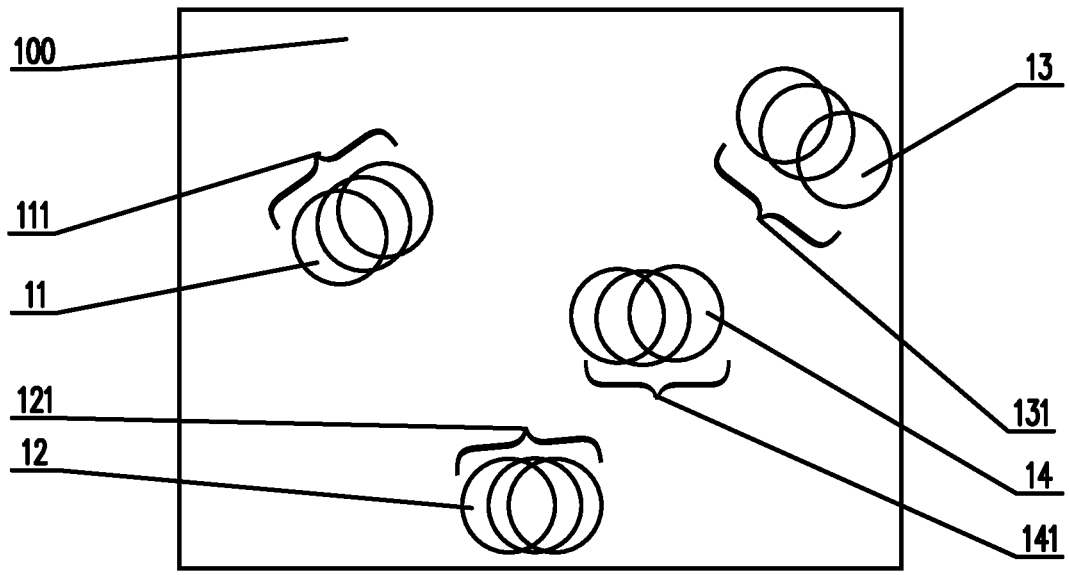
FIG. 2A is a schematic diagram of a superimposed image including a plurality of microbubble trajectories of a plurality of microbubbles according to an embodiment of the present application.

FIG. 2A is a schematic diagram of a superimposed image including a plurality of microbubble trajectories of a plurality of microbubbles according to an embodiment of the present application. As shown in FIG. 2A, the superimposed image 100 is a superimposed image, including four microbubble trajectories of four microbubbles, obtained by superimposing three frames of contrast-enhanced ultrasound images that are in one time interval and each of which includes images of four microbubbles. In the superimposed image 100, the four microbubbles are a microbubble 11, a microbubble 12, a microbubble 13, and a microbubble 14, respectively, and the four microbubble trajectories are a trajectory 111, a trajectory 121, a trajectory 131, and a trajectory 141, respectively.

A quantity of microbubbles in each frame of contrast-enhanced ultrasound images may be selected according to actual requirements, such as imaging accuracy and frame rate as well as another factor. For example, when there is a less quantity of microbubbles in one frame of contrast-enhanced ultrasound images, movement trajectories of the plurality of microbubbles do not easily intersect, which avoids a case in which movement directions of the microbubbles are difficult to distinguish at intersections where the movement trajectories of the plurality of microbubbles intersect, and provides an accurate image of microbubble trajectories for subsequent extraction of information such as the movement directions of the microbubbles, thereby improving flow field reconstruction accuracy. However, a specific quantity of microbubbles are required for flow field reconstruction. When there is a less quantity of images of microbubbles in one frame of contrast-enhanced ultrasound image, a more quantity of frames are required for the flow field reconstruction, and therefore the reconstruction speed of super-resolution flow field is lower. A quantity of images of microbubbles in each frame of contrast-enhanced ultrasound images is not specifically limited in the present application.

In an embodiment, Step 101 may alternatively be: superimposing a plurality of consecutive frames of contrast-enhanced ultrasound images that are in the one time interval and each of which includes the images of the plurality of microbubbles, to obtain the superimposed image including the plurality of microbubble trajectories of the plurality of microbubbles. Superimposing the plurality of consecutive frames of contrast-enhanced ultrasound images may make an overlapping area of the images of the microbubbles larger in the superimposed contrast-enhanced ultrasound images. In addition, there is a uniform moving distance between positions of one microbubble in the consecutive frames, which further improves accuracy of the microbubble trajectories.

In an embodiment, Step 101 may alternatively be: superimposing two, three, or four consecutive frames of contrast-enhanced ultrasound images that are in the one time interval and each of which includes the images of the plurality of microbubbles, to obtain the superimposed image including the plurality of microbubble trajectories of the plurality of microbubbles.

Specifically, a quantity of superimposed frames of the superimposed images may be selected according to an actual situation, for example, may be selected based on parameters such as a microbubble velocity and design precision of the ultrasound imaging system. For example, a shooting frame rate may be increased when the microbubble velocity is relatively high, and the shooting frame rate may be reduced when the microbubble velocity is relatively low, to make sure that the moving distance of a microbubble between consecutive frames is within a specific range. Therefore, the shooting frame rate may be adjusted based on the microbubble velocity, to make sure that the moving distance of a microbubble between consecutive frames is within a specific range. Then, an optimal quantity of superimposed frames is obtained through an experiment in which a distance of a microbubble in a period of one frame is controlled, a variable is set to be a quantity of superimposed frames of the superimposed image, and effects, obtained when different superimposed quantities are set, of microbubble trajectories of the microbubble in the superimposed images are analyzed.

For example, in a super-resolution flow field reconstruction experiment, a distance between image positions of a microbubble in two adjacent frames of overlapped images is controlled to be $\sigma$, that is, a movement distance of the microbubble in a period of one frame is $\sigma$. An image of a microbubble in a contrast-enhanced ultrasound image shot by ultrasound imaging system may be an image of a point spread function, and the point spread function may be regarded as a Gaussian distribution, where a variance of the Gaussian distribution is $\sigma$. However, the size of the point spread function image of the microbubble in the contrast-enhanced ultrasound image shot by the ultrasound imaging system depends on design of an ultrasound probe and imaging parameters set by ultrasound imaging system, for example, the transmitting frequency of the ultrasound probe, the design of transmitting beam, the selected ultrasound beam-forming technique, element spacing of the probe, and other parameters. Therefore, a value of $\sigma$ also depends on the design and the parameters of the ultrasound probe and the ultrasound imaging system. When $\sigma$ is equal to six pixels, two, three, four, and five consecutive frames of contrast-enhanced ultrasound images having a same start frame are separately superimposed, to obtain superimposed images each including a plurality of microbubble trajectories of a plurality of microbubbles, and the superimposed images are shown in FIG. 3A, FIG. 3B, FIG. 3C, and FIG. 3D, respectively.

The value of $\sigma$ may be in a unit of pixel, that is, $\sigma$ may be an analog quantity. According to different application scenarios, the value of $\sigma$ may be in a unit of length in the conventional sense, for example, centimeter or millimeter. The unit of the value of $\sigma$ is not specifically limited in the present application.

Figure 3A:
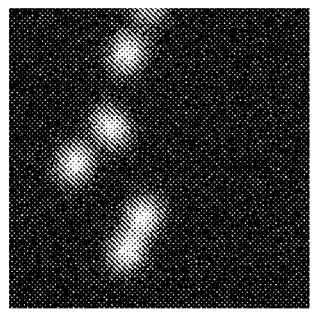
FIG. 3A shows a superimposed image of two consecutive frames of contrast-enhanced ultrasound images according to another embodiment of the present application.
Figure 3B:
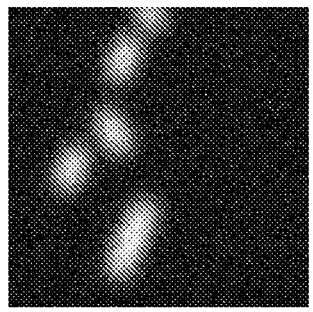
FIG. 3B shows a superimposed image of three consecutive frames of contrast-enhanced ultrasound images according to another embodiment of the present application.
Figure 3C:
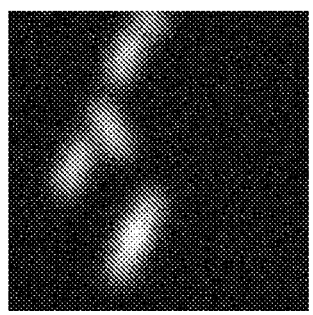
FIG. 3C shows a superimposed image of four consecutive frames of contrast-enhanced ultrasound images according to another embodiment of the present application.
Figure 3D:
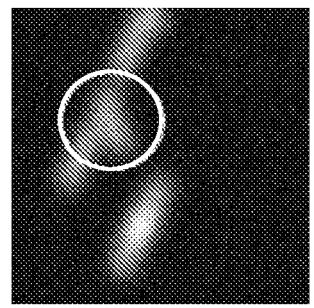
FIG. 3D shows a superimposed image of five consecutive frames of contrast-enhanced ultrasound images according to another embodiment of the present application.

It can be seen that, there are four microbubble trajectories of four microbubbles in each of FIG. 3A, FIG. 3B, and FIG. 3C obtained by superimposing the two, three, and four consecutive frames of contrast-enhanced ultrasound images, respectively. However, at the position indicated by the circle in FIG. 3D, microbubble trajectories of different microbubbles intersect, so that there are at least two directions at an intersection part of the microbubble trajectories, affecting extraction of directions of the microbubble trajectories in subsequent steps, which may cause errors during flow field reconstruction. Therefore, when a distance between image positions of a microbubble in two adjacent frames of overlapped images is $\sigma$, and $\sigma$ is equal to six pixels, two, three, or four consecutive frames of contrast-enhanced ultrasound images that are in one time interval and each of which includes images of the plurality of microbubbles may be superimposed, to obtain the superimposed images each including the plurality of microbubble trajectories without intersection, so that each microbubble trajectory in each superimposed image has a unique direction at each position of the microbubble trajectory, to make preparations for extraction of directions of the microbubble trajectories in subsequent steps, thereby improving accuracy of flow field reconstruction.

When the distance between image positions of a microbubble in two adjacent frames of overlapped images is less than $\sigma$, and $\sigma$ is equal to six pixels, an overlapping area of the images of the microbubble in the two adjacent frames of overlapped images is larger than that obtained when the distance is $\sigma$. Therefore, after a same quantity of frames of contrast-enhanced ultrasound images are superimposed, a microbubble trajectory is shorter than that obtained when the distance is equal to $\sigma$, and a case in which microbubble trajectories intersect is less likely to occur. Therefore, when the distance between image positions of a microbubble in two adjacent frames of overlapped images is less than $\sigma$, and $\sigma$ is equal to six pixels, two, three, or four consecutive frames of contrast-enhanced ultrasound images that are in one time interval and each of which includes images of a plurality of microbubbles may also be superimposed, to obtain superimposed images each including a plurality of microbubble trajectories without intersection.

Figure 4A:
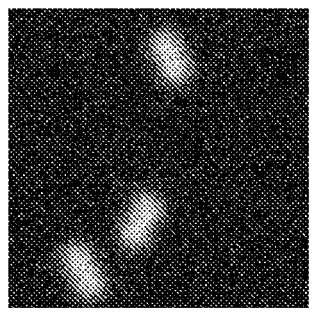
FIG. 4A shows a superimposed image of two consecutive frames of contrast-enhanced ultrasound images according to another embodiment of the present application.

When the distance between image positions of a microbubble in two adjacent frames of overlapped images is $2\sigma$, and $\sigma$ is equal to six pixels, two, three, and four consecutive frames of contrast-enhanced ultrasound images having a same start frame are separately superimposed, to obtain superimposed images each including a plurality of microbubble trajectories of a plurality of microbubbles, and the superimposed images are shown in FIG. 4A, FIG. 4B, and FIG. 4C, respectively.

It can be seen that, there are three microbubble trajectories of three microbubbles in each of FIG. 4A and FIG. 4B obtained by superimposing the two and three consecutive frames of contrast-enhanced ultrasound images, respectively. However, at the position indicated by the circle in FIG. 4C, microbubble trajectories of different microbubbles intersect, so that there are at least two directions at an intersection part of the microbubble trajectories, affecting extraction of directions of the microbubble trajectories in subsequent steps, which may cause errors during flow field reconstruction. Therefore, when the distance between image positions of a microbubble in two adjacent frames of overlapped images is $2\sigma$, and $\sigma$ is equal to six pixels, two or three consecutive frames of contrast-enhanced ultrasound images that are in one time interval and each of which includes images of the plurality of microbubbles may be superimposed, to obtain the superimposed images each including the plurality of microbubble trajectories without intersection, so that each microbubble trajectory has a unique direction at each position of the microbubble trajectory, to make preparations for extraction of directions of the microbubble trajectories in subsequent steps, thereby improving accuracy of flow field reconstruction.

When the distance between image positions of a microbubble in two adjacent frames of overlapped images is less than 2σ, and σ is equal to six pixels, an overlapping area of the images of the microbubble in the two adjacent frames of overlapped images is larger than that obtained when the distance is 2σ. Therefore, after a same quantity of frames of contrast-enhanced ultrasound images are superimposed, a microbubble trajectory is shorter than that obtained when the distance is equal to 2σ, and a case in which microbubble trajectories intersect is less likely to occur. In addition, when the distance between image positions of a microbubble in two adjacent frames of overlapped images is less than 2σ, and σ is equal to six pixels, two or three consecutive frames of contrast-enhanced ultrasound images that are in one time interval and each of which includes images of a plurality of microbubbles may also be superimposed, to obtain superimposed images each including a plurality of microbubble trajectories without intersection.

Step 102: performing straight line fitting on the plurality of microbubble trajectories, to obtain a plurality of microbubble trajectory straight lines of the plurality of microbubbles, respectively.

Figure 2B:
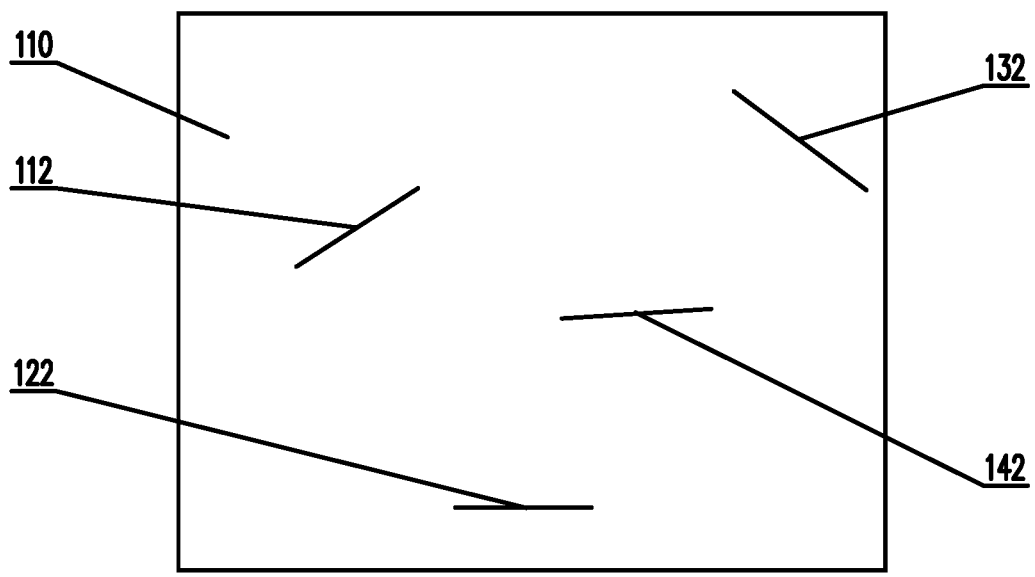
FIG. 2B is a schematic diagram of an image including a plurality of microbubble trajectory straight lines of a plurality of microbubbles according to an embodiment of the present application.

Specifically, the straight line fitting may be performed on the trajectory 111, the trajectory 121, the trajectory 131, and the trajectory 141 shown in FIG. 2A, to obtain the superimposed image 110 including the trajectory straight line 112, the trajectory straight line 122, the trajectory straight line 132, and the trajectory straight line 142, as shown in FIG. 2B.

In an embodiment, the straight line fitting may be performed by using a Hough transform-based straight line detection method. Owing to strong anti-noise and anti-deformation capabilities of the Hough transform-based straight line detection method, a trajectory straight line corresponding to a trajectory may be extracted more accurately.

Step 103: determining, based on directions and lengths of the plurality of microbubble trajectory straight lines of the plurality of microbubbles and a quantity of superimposed frames and a frame rate of the plurality of frames of contrast-enhanced ultrasound images, directions and velocities of instantaneous movements of the plurality of microbubbles in the time interval.

Specifically, since the microbubble trajectory straight line of the microbubble is obtained through line fitting process after the plurality of frames of contrast-enhanced ultrasound images in one time interval are superimposed, the microbubble trajectory straight line of the microbubble may be a movement trajectory of the microbubble in the time interval of the plurality of frames of contrast-enhanced ultrasound images. Therefore, a movement direction and a movement velocity of the microbubble at any position of the microbubble trajectory straight line are the movement direction and velocity of an instantaneous movement of the microbubble, respectively.

In an embodiment, the directions of instantaneous movements of the plurality of microbubbles in the time interval may be determined based on the directions of the microbubble trajectory straight lines of the plurality of microbubbles. The velocities of instantaneous movements of the plurality of microbubbles in the time interval are determined based on a product of the frame rate and a ratio of the lengths of the microbubble trajectory straight lines of the plurality of microbubbles to the quantity of superimposed frames of the plurality of frames of contrast-enhanced ultrasound images.

Specifically, a movement direction of the microbubble at any position of the trajectory straight line is the direction of an instantaneous movement of the microbubble, that is, a direction of the microbubble trajectory straight line of the microbubble is the direction of the instantaneous movement of the microbubble. A length of the microbubble trajectory straight line of the microbubble may be a length of a movement trajectory of the microbubble in a time interval of a plurality of frames of contrast-enhanced ultrasound images, namely, a movement distance of the microbubble. The quantity of superimposed frames of the plurality of frames of contrast-enhanced ultrasound images may be a movement time interval of the microbubble, so that a movement velocity of the microbubble is a ratio of the movement distance to the movement time interval of the microbubble. Therefore, velocities of instantaneous movements of a plurality of microbubbles in a time interval may be a product of a frame rate and a ratio of lengths of microbubble trajectory straight lines of the plurality of microbubbles to a quantity of superimposed frames of a plurality of frames of contrast-enhanced ultrasound images.

Figure 2C:
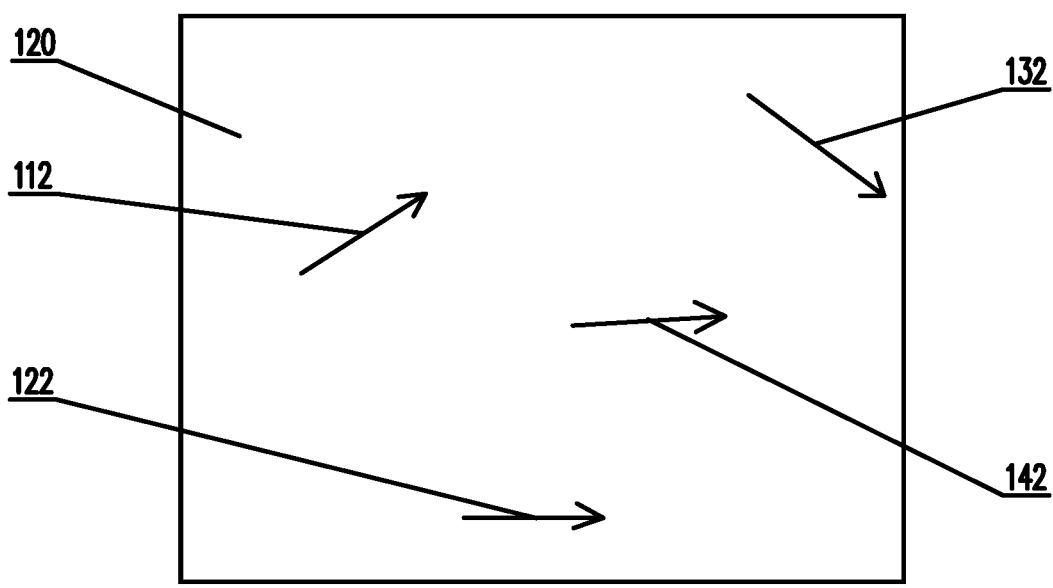
FIG. 2C is a schematic diagram of an image including directions of a plurality of microbubble trajectory straight lines of a plurality of microbubbles according to an embodiment of the present application.

For example, as shown in FIG. 2C, a direction of each of the trajectory straight line 112, the trajectory straight line 122, the trajectory straight line 132, and the trajectory straight line 142, namely, a direction indicated by an arrow of each trajectory straight line in the superimposed image 120 shown in FIG. 2C, may be a movement direction of a microbubble at any position of the trajectory straight line, namely, a direction of an instantaneous movement of the microbubble. For example, a shooting frame rate is set to be 1 frame per second (FPS), and a velocity of an instantaneous movement of the microbubble 11 may be a product of a frame rate of 1 FPS and a ratio of the length of the trajectory straight line 112 to a quantity of superimposed frames 3. If the length of the trajectory straight line 112 is 6 cm, the velocity of the instantaneous movement of the microbubble is a product of 1 FPS and a ratio of 6 cm to the quantity of superimposed frames 3, namely 2 cm/s.

Step 104: reconstructing a super-resolution flow field based on directions and velocities of instantaneous movements of the plurality of microbubbles in each of different time intervals.

Specifically, the directions and velocities of the instantaneous movements, in the one time interval, of the plurality of microbubbles are obtained through Step 101 to Step 103. Step 101 to Step 103 are repeated to obtain the directions and velocities of the instantaneous movements, in different time intervals, of the plurality of microbubbles. Since a movement trajectory of a microbubble is formed along the shape of a flow field, the directions and velocities of the instantaneous movements of the microbubbles in a plurality of different time intervals may form a plurality of movement trajectories of the plurality of microbubbles, that is, may form a part of a shape of a flow field. When a proper quantity of different time intervals is selected, a complete shape of a flow field may be formed.

A quantity of different time intervals may be selected according to an actual requirement. For example, a quantity of different time intervals in which directions and velocities of instantaneous movements of microbubbles are used to obtain a required part of a flow field may be estimated based on a microbubble velocity. The quantity of different time intervals is not specifically limited in the present application.

It can be learned that, according to a super-resolution flow field reconstruction method provided in the embodiment of the present application, parameters of instantaneous movements of the plurality of microbubbles in the one time interval are calculated by utilizing trajectories formed in the plurality of frames of superimposed contrast-enhanced ultrasound images of the plurality of microbubbles in the time interval, and the super-resolution flow field is then reconstructed based on parameters of instantaneous movements of the plurality of microbubbles in each of the different time intervals, which avoids tracking and positioning of the plurality of moving microbubbles, overcomes the limitations of current ultrasound super-resolution imaging strategies under the impact of motion artifacts and low signal-to-noise-ratio, and improves precision and efficiency of super-resolution flow field reconstruction.

FIG. 5 is a schematic flowchart diagram of a super-resolution flow field reconstruction method according to another embodiment of the present application. As shown in FIG. 5, the superimposing a plurality of frames of contrast-enhanced ultrasound images that are in one time interval and each of which includes images of a plurality of microbubbles, to obtain a superimposed image including a plurality of microbubble trajectories of the plurality of microbubbles includes the following steps.

Step 501: performing registration on the plurality of frames of contrast-enhanced ultrasound images that are in the one time interval and each of which includes the images of the plurality of microbubbles, to obtain a plurality of frames of registered contrast-enhanced ultrasound images each including the images of the plurality of microbubbles.

Specifically, performing registration on the contrast-enhanced ultrasound images may eliminate tissue movement artifacts, so that the contrast-enhanced ultrasound images are superimposed more accurately in the next step. During the acquisition of contrast-enhanced ultrasound images, in addition to microbubbles, tissues such as muscle and fat tend to move slightly during breath. Therefore, performing registration on the contrast-enhanced ultrasound images may eliminate tissue movement artifacts and reduce image distortion caused by tissue movement, so that the contrast-enhanced ultrasound images are superimposed more accurately in the next step.

In an embodiment, image registration may be performed by using a Morphon multi-scale registration method, in which three layers of decomposition may be selected according to decomposition scale: global decomposition, local decomposition, and detail decomposition. The global decomposition may refer to identifying a deformation field of a contrast-enhanced ultrasound image as a whole, and performing Gaussian kernel smoothing on the deformation field. The local decomposition may refer to identifying a deformation field of a contrast-enhanced ultrasound image from a local part, and performing Gaussian kernel smoothing on the deformation field. The detail decomposition may refer to identifying a deformation field of a contrast-enhanced ultrasound image from some detailed characteristics, and performing Gaussian kernel smoothing on the deformation field. In an embodiment, a size of a Gaussian kernel may be 10 pixels.

A smoothing degree and size of the Gaussian kernel may be selected according to an actual application requirement, for example, registration accuracy and a registration speed. The smoothing degree and size of the Gaussian kernel are not specifically limited in the present application.

Step 502: superimposing the plurality of frames of registered contrast-enhanced ultrasound images that are in the one time interval and each of which includes the images of the plurality of microbubbles, to obtain the superimposed image including the plurality of microbubble trajectories of the plurality of microbubbles.

Specifically, superimposing the registered contrast-enhanced ultrasound images may make the superimposed image including the plurality of microbubble trajectories of the plurality of microbubbles obtained more accurately.

FIG. 6 is a schematic flowchart diagram of a super-resolution flow field reconstruction method according to another embodiment of the present application. As shown in FIG. 6, the superimposing a plurality of frames of contrast-enhanced ultrasound images that are in one time interval and each of which includes images of a plurality of microbubbles, to obtain a superimposed image including a plurality of microbubble trajectories of the plurality of microbubbles may include the following steps.

Step 601: superimposing the plurality of frames of contrast-enhanced ultrasound images that are in the one time interval and each of which includes the images of the plurality of microbubbles, to obtain a superimposed image including a plurality of preliminary microbubble trajectories of the plurality of microbubbles.

Figure 7A:
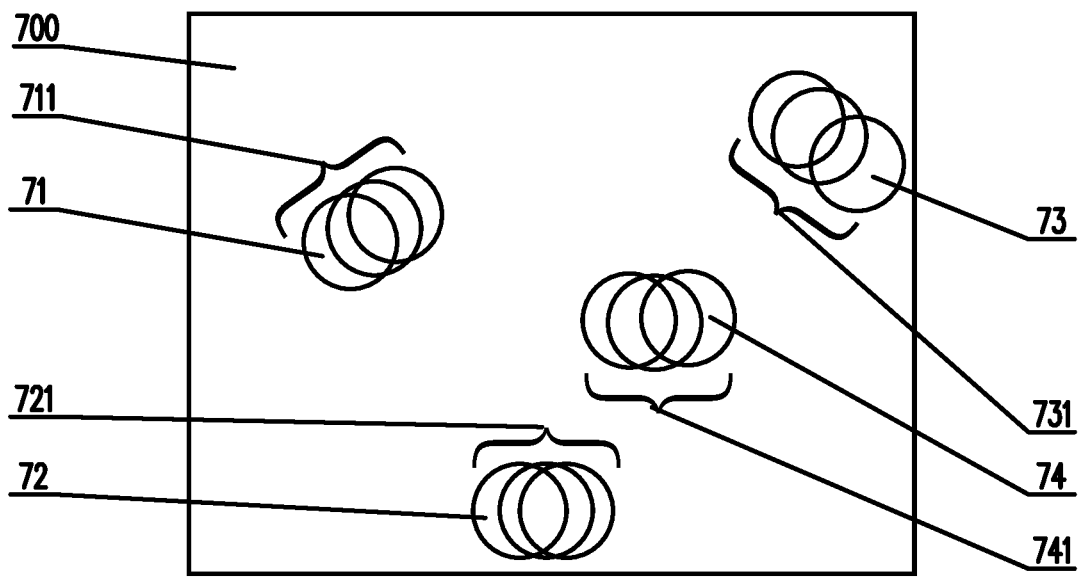
FIG. 7A is a schematic diagram of a superimposed image including a plurality of preliminary microbubble trajectories according to another embodiment of the present application.

Specifically, three frames of contrast-enhanced ultrasound images that are in one time interval and each of which includes images of four microbubbles are superimposed, to obtain a superimposed image 600 including four preliminary microbubble trajectories of the four microbubbles, and the superimposed image 600 is shown in FIG. 7A. The four microbubbles are a microbubble 71, a microbubble 72, a microbubble 73, and a microbubble 74, respectively, and the four preliminary microbubble trajectories are a preliminary microbubble trajectory 711, a preliminary microbubble trajectory 721, a preliminary microbubble trajectory 731, and a preliminary microbubble trajectory 741, respectively. Contours of the microbubbles at superimposed parts are merged after the microbubbles are superimposed. Therefore, the superimposed image 710 including four preliminary microbubble trajectories with only outermost contours is actually obtained, as shown in FIG. 7B.

Step 602: separately performing skeleton extraction on the plurality of preliminary microbubble trajectories in the superimposed image, to obtain the plurality of microbubble trajectories.

Specifically, the skeleton extraction refers to generating, by using a data processing and calculation method, lines that may represent shapes of preliminary microbubble trajectories and using these lines as a skeleton. In an embodiment, the skeleton extraction may be extracting a middle axis from a graph by using a geometric operation method. For example, a middle axis of a rectangle is a central axis of the rectangle along a long side, and performing the skeleton extraction on the preliminary microbubble trajectories may be extracting central axes of the preliminary microbubble trajectories along directions of the trajectories.

Figure 7B:
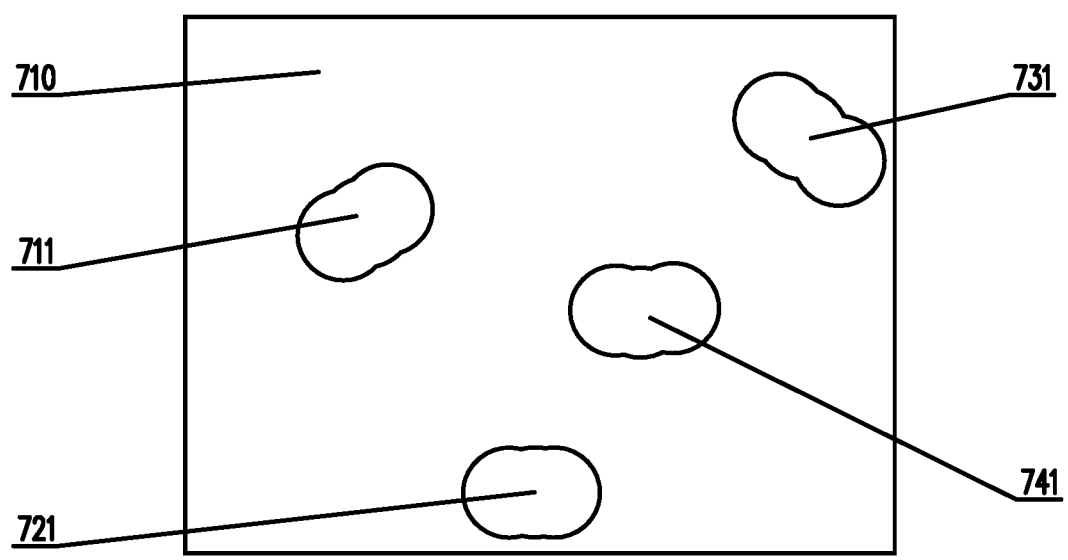
FIG. 7B is a schematic diagram of a superimposed image including a plurality of preliminary microbubble trajectory contours according to another embodiment of the present application.

For example, the skeleton extraction is separately performed on the four preliminary microbubble trajectories in the superimposed image shown in FIG. 7B, to obtain a superimposed image 720 including four microbubble trajectories, as shown in FIG. 7C. The four microbubble trajectories are a microbubble trajectory 712, a microbubble trajectory 722, a microbubble trajectory 732, and a microbubble trajectory 742, respectively. Performing the skeleton extraction on the preliminary microbubble trajectories eliminates the diffraction effect of the preliminary microbubble trajectories, increases resolution of the microbubble trajectories, and breaks the resolution limit of the ultrasound imaging system, so that microbubble trajectories with higher accuracy are obtained.

In an embodiment, the skeleton extraction may be separately performed on the plurality of preliminary microbubble trajectories in the superimposed image by using an iterative erosion algorithm. The iterative erosion algorithm is implemented by identifying a boundary of a graph and subtracting the boundary of the graph from the original graph to obtain a refined graph. After the foregoing refinement is repeated for a plurality of times, a final graph is obtained. The algorithm is simple, and the calculation speed is fast.

In an embodiment, the skeleton extraction may be separately performed on the plurality of preliminary microbubble trajectories in the superimposed image by using a circumscribed rectangle-maximum grayscale integral axis extraction algorithm. The circumscribed rectangle-maximum grayscale integral axis extraction algorithm mainly includes the following steps: calculating a maximum circumscribed rectangle of each preliminary microbubble trajectory, which is equivalent to placing each preliminary microbubble trajectory in a circumscribed rectangle; then extracting four axes of the rectangle (namely, four symmetric lines of the rectangle); performing summing on gray-scale values of pixels that each axis passes through, to obtain a grayscale integral value corresponding to each axis; and finally, selecting the axis with a maximum grayscale integral value and using the axis as a skeleton. The circumscribed rectangle-maximum grayscale integral axis extraction algorithm may be used to extract an axis based on different grayscale integral values. Therefore, a skeleton of a graph may be extracted more accurately.

FIG. 8 is a schematic flowchart diagram of a super-resolution flow field reconstruction method according to another embodiment of the present application. As shown in FIG. 8, the reconstructing a super-resolution flow field based on directions and velocities of instantaneous movements of the plurality of microbubbles in each of different time intervals may include the following steps.

Step 801: determining, based on the directions and velocities of instantaneous movements of the plurality of microbubbles in each of the different time intervals, directions and velocities of instantaneous movements of the plurality of microbubbles, in each of the different time intervals, corresponding to a plurality of pixel coordinates.

Specifically, each microbubble trajectory straight line of each microbubble in the plurality of microbubble trajectory straight lines of the plurality of microbubbles includes at least one pixel coordinate. For example, compared to the superimposed image 110 shown in FIG. 2B including the trajectory straight line 112, the trajectory straight line 122, the trajectory straight line 132, and the trajectory straight line 142, in a superimposed image 900 shown in FIG. 9 including a trajectory straight line 910, a trajectory straight line 920, a trajectory straight line 930, and a trajectory straight line 940, each trajectory straight line includes at least one pixel. For example, the trajectory straight line 910 includes a pixel 911, the trajectory straight line 920 includes a pixel 921, a pixel 922, and a pixel 923, the trajectory straight line 930 includes a pixel 931 and a pixel 932, and the trajectory straight line 940 includes a pixel 941, a pixel 942, a pixel 943, and a pixel 944.

Since the microbubble trajectory straight line of the microbubble is obtained through line fitting after the plurality of frames of contrast-enhanced ultrasound images in the one time interval are superimposed, the microbubble trajectory straight line of the microbubble may be a movement trajectory of the microbubble in the time interval of the plurality of frames of contrast-enhanced ultrasound images. Therefore, the movement direction and velocity of the microbubble at any position of the trajectory straight line are a direction and velocity of an instantaneous movement of microbubble, respectively. A direction and velocity of an instantaneous movement of a microbubble corresponding to coordinates of a pixel are respectively equal to a direction and velocity of an instantaneous movement of the microbubble on a corresponding microbubble trajectory straight line in a corresponding time interval. For example, a direction and velocity of an instantaneous movement of a microbubble corresponding to coordinates of the pixel 911 are respectively equal to a direction and velocity of an instantaneous movement of the microbubble on the trajectory straight line 910 in a corresponding time interval.

Step 802: reconstructing the super-resolution flow field based on the directions and velocities of instantaneous movements of the plurality of microbubbles, in each of the different time intervals, corresponding to the plurality of pixel coordinates.

Specifically, the directions and velocities of instantaneous movements of the plurality of microbubbles, in each of the different time intervals, corresponding to the plurality of pixel coordinates are obtained in Step 801. Since the movement trajectory of the microbubble is the shape of the flow field, the directions and velocities of instantaneous movements of the microbubbles in the plurality of different time intervals may form the plurality of movement trajectories of the plurality of microbubbles, that is, may form a part of the shape of the flow field. When a proper quantity of different time intervals is selected, a complete shape of the flow field may be formed.

Figure 10A:
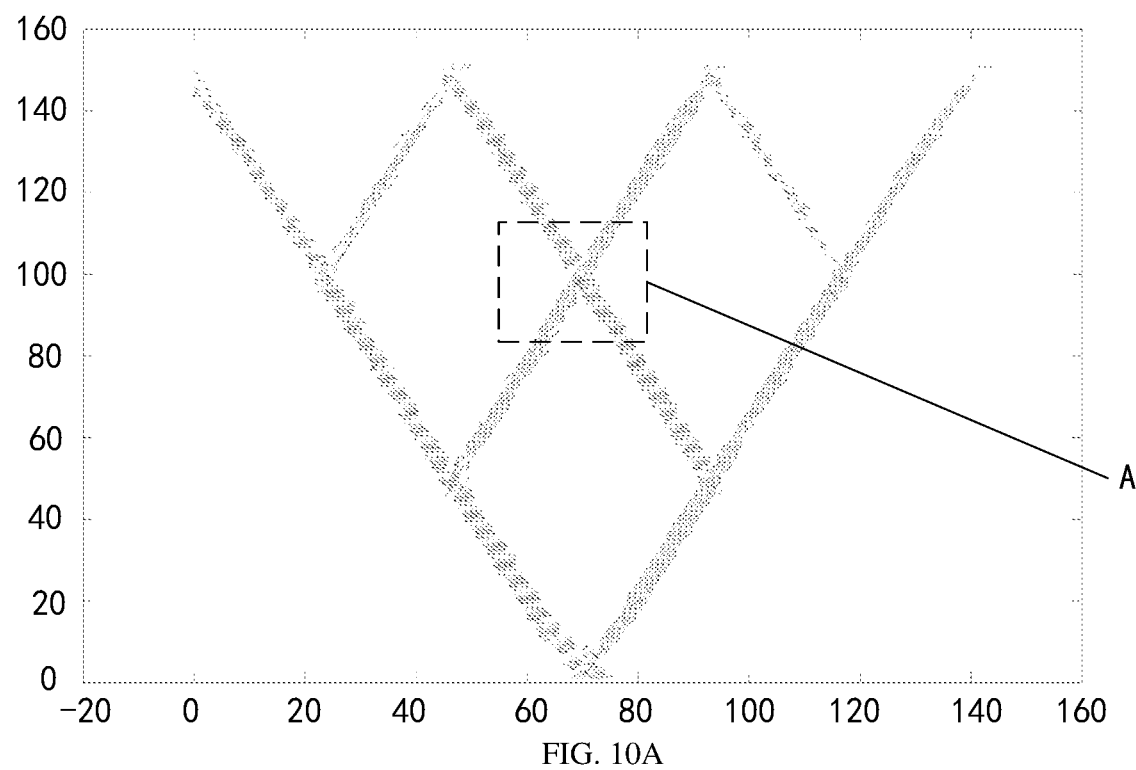
FIG. 10A is a super-resolution flow field diagram according to another embodiment of the present application.
Figure 10B:
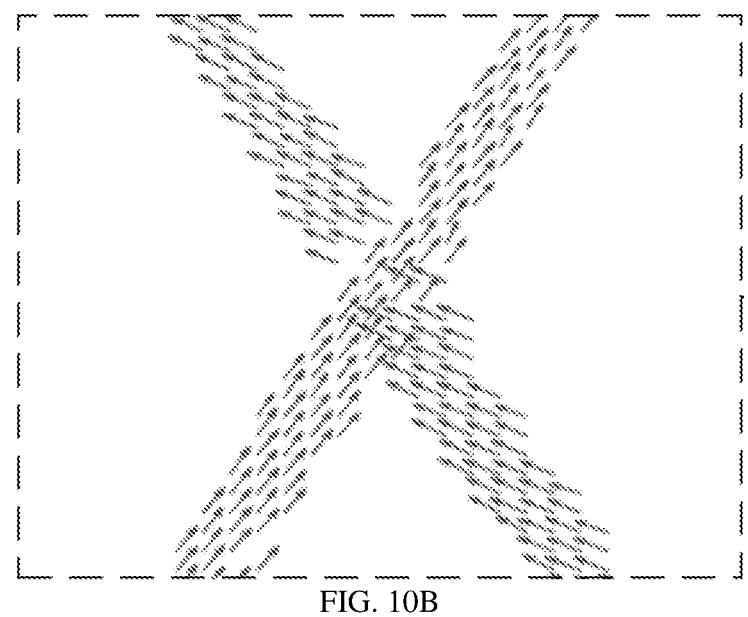
FIG. 10B is a partial enlarged view of the region A of the super-resolution flow field diagram in FIG. 10A.

FIG. 10A is a super-resolution flow field diagram according to another embodiment of the present application. FIG. 10B is a partial enlarged view of the region A of the super-resolution flow field diagram in FIG. 10A. FIG. 10A is a complete super-resolution flow field diagram. To show detailed characteristics of the flow field in FIG. 10A more clearly, a local part of FIG. 10A is arbitrarily intercepted and enlarged to obtain FIG. 10B. In FIG. 10B, a plurality of arrows may be seen more clearly. Each arrow represents a direction and velocity of an instantaneous movement of a microbubble corresponding to coordinates of a pixel, namely a velocity vector of the instantaneous movement of the microbubble.

Since the trajectory straight lines of a same microbubble may include same pixel coordinates in different time intervals, the more pixels a trajectory straight line includes, the more quantities of directions and velocities of instantaneous movements of a microbubble the trajectory straight line corresponds to. When the quantities of directions and velocities of the instantaneous movements of the microbubble reach a specific value, flow field reconstruction may be completed. Therefore, the more pixels a trajectory straight line includes, the higher the reconstruction efficiency of the super-resolution flow field is.

In an embodiment, there may be an interval of a same quantity of frames between start frames in different time intervals. However, the different time intervals include a same quantity of frames. For example, a time interval 1 includes the first frame to the third frame, a time interval 2 includes the second frame to the fourth frame, and a time interval 3 includes the third frame to the fifth frame, that is, there is an interval of one frame between the start frames in every two adjacent time intervals. Start frames in every two adjacent time intervals have an interval of a same quantity of frames, so that there is a uniform distance between trajectory straight lines corresponding to the same microbubble in the superimposed image of a plurality of time intervals.

In an embodiment, the super-resolution flow field may be reconstructed by using a highest frequency-based method. Specifically, a frequency of occurrence of each of directions and velocities of instantaneous movements corresponding to same pixel coordinates of each microbubble on different trajectory straight lines is calculated, and a direction and velocity, having a highest frequency of occurrence, of instantaneous movements are selected and used to form arrows that are used to represent directions and velocities, both having the highest frequency of occurrence, of instantaneous movements of each microbubble at coordinates of each same pixel into a same image, to form the super-resolution flow field diagram.

In an embodiment, the super-resolution flow field may be reconstructed by using an average value-based method. Specifically, an average value of each of directions and velocities of instantaneous movements corresponding to same pixel coordinates of each microbubble on different trajectory straight lines is calculated, to obtain an average direction and velocity of instantaneous movements of each microbubble, and the average direction and velocity are used to form arrows that are used to represent average directions and average velocities of instantaneous movements of each microbubble at coordinates of each same pixel into a same image, to form the super-resolution flow field diagram.

In an embodiment, the super-resolution flow field may be reconstructed by using a maximum value-based method. Specifically, a maximum value of each of directions and velocities of instantaneous movements corresponding to same pixel coordinates of each microbubble on different trajectory straight lines is calculated and used to form arrows that are used to represent maximum direction angles and maximum velocities of instantaneous movements of each microbubble at coordinates of each same pixel into a same image, to form the super-resolution flow field diagram.

Methods of reconstructing the super-resolution flow field are not limited to the highest frequency-based method, the average value-based method, and the maximum value-based method, and may be selected according to a specific application requirement, which is not specifically limited in the present application.

Exemplary Super-Resolution Flow Field Reconstruction Devices

Figure 11:
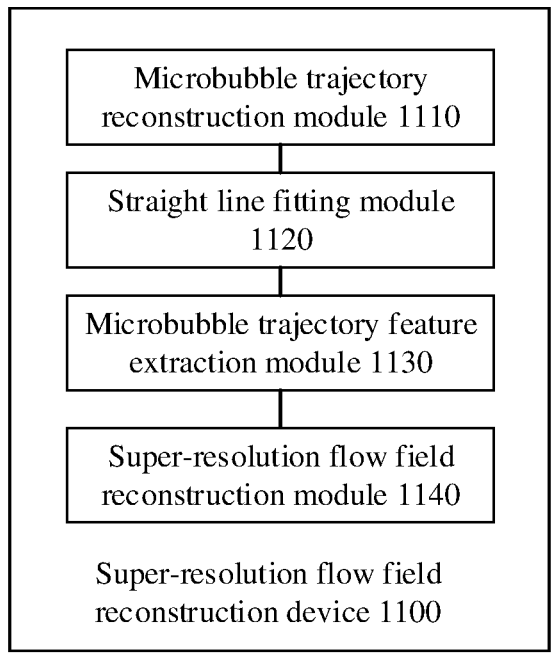
FIG. 11 is a schematic structural diagram of a super-resolution flow field reconstruction device according to an embodiment of the present application.

FIG. 11 is a schematic structural diagram of a super-resolution flow field reconstruction device according to an embodiment of the present application. As shown in FIG. 11, the super-resolution flow field reconstruction device 1100 includes the following modules.

A microbubble trajectory reconstruction module 1110, configured to superimpose a plurality of frames of contrast-enhanced ultrasound images that are in one time interval and each of which includes images of a plurality of microbubbles, to obtain a superimposed image including a plurality of microbubble trajectories of the plurality of microbubbles.

A straight line fitting module 1120, configured to perform straight line fitting on the plurality of microbubble trajectories, to obtain a plurality of microbubble trajectory straight lines of the plurality of microbubbles, respectively.

A microbubble trajectory feature extraction module 1130, configured to determine, based on directions and lengths of the plurality of microbubble trajectory straight lines and a quantity of superimposed frames and a frame rate of the plurality of frames of contrast-enhanced ultrasound images, directions and velocities of instantaneous movements of the plurality of microbubbles in the time interval.

A super-resolution flow field reconstruction module 1140, configured to reconstruct a super-resolution flow field based on directions and velocities of instantaneous movements of the plurality of microbubbles in each of different time intervals.

In an embodiment, the microbubble trajectory reconstruction module 1110 may be further configured to superimpose a plurality of consecutive frames of contrast-enhanced ultrasound images that are in the one time interval and each of which includes the images of the plurality of microbubbles, to obtain the superimposed image including the plurality of microbubble trajectories of the plurality of microbubbles.

In an embodiment, the microbubble trajectory reconstruction module 1110 may be further configured to superimpose two, three, or four consecutive frames of contrast-enhanced ultrasound images that are in the one time interval and each of which includes the images of the plurality of microbubbles, to obtain the superimposed image including the plurality of microbubble trajectories of the plurality of microbubbles.

In an embodiment, the microbubble trajectory feature extraction module 1130 may be further configured to: determine, based on the directions of the plurality of microbubble trajectory straight lines of the plurality of microbubbles, the directions of instantaneous movements of the plurality of microbubbles in the time interval; and determine, based on a product of the frame rate and a ratio of the lengths of the microbubble trajectory straight lines of the plurality of microbubbles to the quantity of superimposed frames of the plurality of frames of contrast-enhanced ultrasound images, the velocities of instantaneous movements of the plurality of microbubbles in the time interval.

In an embodiment, the super-resolution flow field reconstruction module 1140 may be further configured to reconstruct the super-resolution flow field based on directions and velocities of instantaneous movements of the plurality of microbubbles in each of different time intervals that include a same quantity of frames and whose start frames have a same interval.

In an embodiment, each microbubble trajectory straight line of each microbubble in the plurality of microbubble trajectory straight lines of the plurality of microbubbles includes at least one pixel coordinate. The super-resolution flow field reconstruction module 1140 may be further configured to determine, based on the directions and velocities of instantaneous movements of the plurality of microbubbles in each of the different time intervals, directions and velocities of instantaneous movements of the plurality of microbubbles, in each of the different time intervals, corresponding to a plurality of pixel coordinates; and reconstruct the super-resolution flow field based on the directions and velocities of instantaneous movements of the plurality of microbubbles, in each of the different time intervals, corresponding to the plurality of pixel coordinates.

In an embodiment, the super-resolution flow field reconstruction module 1140 may be further configured to: calculate a frequency of occurrence of each of directions and velocities of instantaneous movements corresponding to the same pixel coordinates of the each microbubble, and select a direction and a velocity, having the highest frequency of occurrence, of instantaneous movements to reconstruct the super-resolution flow field.

In an embodiment, the super-resolution flow field reconstruction module 1140 may be further configured to calculate an average value of each of directions and velocities of instantaneous movements corresponding to the same pixel coordinates of the each microbubble, to reconstruct the super-resolution flow field.

In an embodiment, the super-resolution flow field reconstruction module 1140 may be further configured to calculate a maximum value of each of directions and velocities of instantaneous movements corresponding to the same pixel coordinates of the each microbubble to reconstruct the super-resolution flow field.

Figure 12:
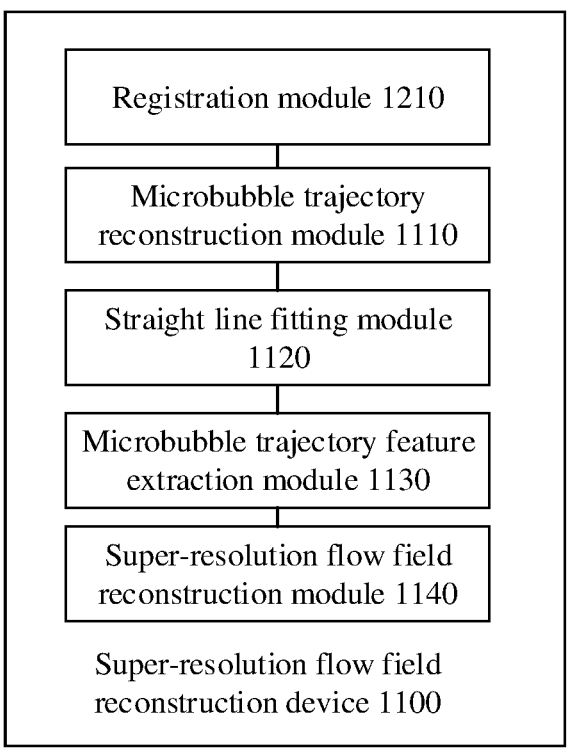
FIG. 12 is a schematic structural diagram of a super-resolution flow field reconstruction device according to another embodiment of the present application.

FIG. 12 is a schematic structural diagram of a super-resolution flow field reconstruction device according to another embodiment of the present application. As shown in FIG. 12, the super-resolution flow field reconstruction device 1100 further includes the following module.

A registration module 1210, configured to perform registration on the plurality of frames of contrast-enhanced ultrasound images that are in the one time interval and each of which includes images of a plurality of microbubbles, to obtain a plurality of frames of registered contrast-enhanced ultrasound images each including the images of the plurality of microbubbles.

Figure 13:
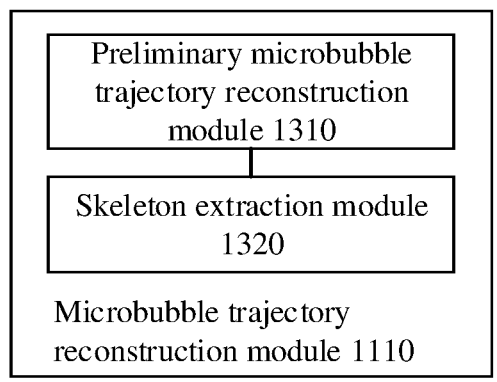
FIG. 13 is a schematic structural diagram of a microbubble trajectory reconstruction module according to another embodiment of the present application.

In an embodiment, as shown in FIG. 13, the microbubble trajectory reconstruction module 1110 includes the following modules.

A preliminary microbubble trajectory reconstruction module 1310, configured to superimpose the plurality of frames of contrast-enhanced ultrasound images that are in the one time interval and each of which includes the images of the plurality of microbubbles, to obtain a superimposed image including a plurality of preliminary microbubble trajectories of the plurality of microbubbles.

A skeleton extraction module 1320, configured to separately perform skeleton extraction on the plurality of preliminary microbubble trajectories in the superimposed image, to obtain the plurality of microbubble trajectories.

In an embodiment, the skeleton extraction module 1320 may be further configured to separately perform, by using an iterative erosion algorithm, the skeleton extraction on the plurality of preliminary microbubble trajectories in the superimposed image, to obtain the plurality of microbubble trajectories.

In an embodiment, the skeleton extraction module 1320 may be further configured to separately perform, by using a circumscribed rectangle-maximum grayscale integral axis extraction algorithm, the skeleton extraction on the plurality of preliminary microbubble trajectories in the superimposed image, to obtain the plurality of microbubble trajectories.

It should be noted that the super-resolution flow field reconstruction device 1100 provided in the embodiment of the present application may be integrated into an electronic device 1400 as a software module and/or a hardware module. In other words, the electronic device 1400 may include the super-resolution flow field reconstruction device 1100. For example, the super-resolution flow field reconstruction device 1100 may be a software module in the operating system of the electronic device 1400, or may be an application developed for super-resolution flow field reconstruction. Certainly, the super-resolution flow field reconstruction device 1100 may alternatively be one of many hardware modules of the electronic device 1400.

In another embodiment of the present application, the super-resolution flow field reconstruction device 1100 may alternatively be a device (for example, a server) separate from the electronic device 1400, and the super-resolution flow field reconstruction device 1100 may be connected to the electronic device 1400 via a wired network and/or a wireless network, and transmit interaction information according to an agreed data format.

Exemplary Electronic Device

Figure 14:
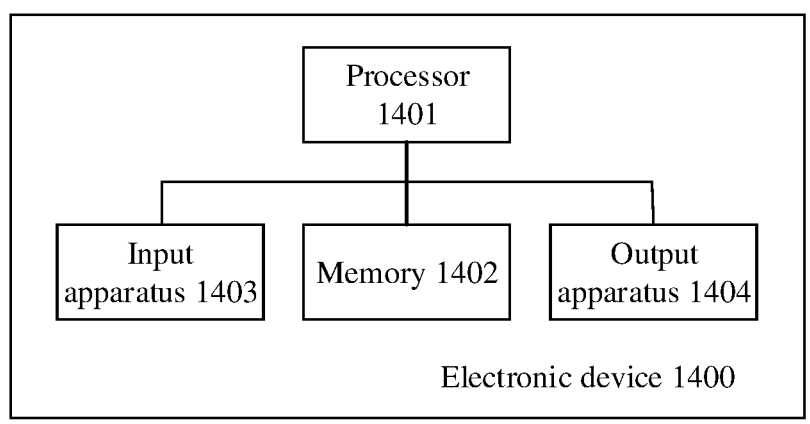
FIG. 14 is a schematic structural diagram of an electronic device according to an embodiment of the present application.

FIG. 14 is a schematic structural diagram of an electronic device according to an embodiment of the present application. As shown in FIG. 14, the electronic device 1400 includes: one or more processors 1401; and a memory 1402, where the memory 1402 stores computer program instructions, and when the computer program instructions are run by the processor 1401, the processor 1401 is enabled to execute the super-resolution flow field reconstruction method according to any one of the foregoing embodiments.

The processor 1401 may be a Central Processing Unit (CPU) or a processing unit in another form that has a data handling capacity and/or instruction execution capacity, and may control another component in the electronic device to perform a desired function.

The memory 1402 may include one or more computer program products. The computer program product may include computer-readable storage media in various forms, for example, a volatile memory and/or a nonvolatile memory. The volatile memory may include, for example, a Random Access Memory (RAM) and/or a cache memory (cache). The nonvolatile memory may include, for example, a Read-Only Memory (ROM), a hard disk, and a flash memory. The computer-readable storage medium may store one or more computer program instructions. The processor 1401 may run the program instructions, to implement steps in the super-resolution flow field reconstruction methods of the foregoing embodiments in the present application and/or another desired function. The computer-readable storage medium may also store information such as a contrast-enhanced ultrasound image and a velocity of a microbubble.

In an example, the electronic device 1400 may further include an input device 1403 and an output device 1404. These components may be interconnected to each other by using a bus system and/or a connecting mechanism in another form (not shown in the FIG. 14).

For example, when the electronic device is, for example, an ultrasound imaging system, the input device 1403 may be an ultrasound probe configured to detect a position of a microbubble. When the electronic device is single unit equipment, the input device 1403 may be a communication network connector, configured to receive a collected input signal from an external movable device. In addition, the input device 1403 may further include, for example, a keyboard, a mouse, and a microphone.

The output device 1404 may output various information to an external device. For example, the output device 1404 may include, for example, a display, a speaker, a printer, a communication network, and a remote output device connected to it, and so on.

Certainly, for simplicity, FIG. 14 only shows some of components in the electronic device 1400 that are related to the present application, and does not show components such as a bus, an input device/an output interface. In addition, according to a specific application situation, the electronic device 1400 may further include another proper component.

Exemplary Computer Program Products and Computer-Readable Storage Media

In addition to the foregoing methods and devices, an embodiment of the present application may alternatively be a computer program product. The computer program product includes computer program instructions. When the computer program instructions are run by a processor, the processor is enabled to perform steps of the super-resolution flow field reconstruction method according to any one of the foregoing embodiments.

The computer program product may use any combination of one or more programming languages to write a program code for performing operations in the embodiments of the present application. The programming languages include an object oriented programming language such as Java, and C++, and further include a conventional procedural programming language, such as the "C" language or a similar programming language. The program code may be entirely executed on a user's computing device, partially on a user's computing device, executed as an independent software package, partially executed on a user's computing device and partially executed on a remote computing device, or entirely executed on a remote computing device or a server.

In addition, the embodiments of the present application may alternatively be computer-readable storage mediums. The computer-readable storage medium stores computer program instructions. When the computer program instructions are run by a processor, the processor is enabled to perform the steps of the super-resolution flow field reconstruction method according to the embodiments of the present application described in section "Exemplary Super-Resolution Flow Field Reconstruction Methods" of this specification.

The computer-readable storage medium may use any combination of one or more readable media. The readable medium may be a readable signal medium or readable storage medium. The readable storage medium may include, for example, but not limited to, an electronic, magnetic, optical, electromagnetic, infrared, or semiconductor system, device, or means, or any combination of the above. More specific examples (a non-exhaustive list) of the readable storage medium include an electrical connection having one or more wires, a portable computer disk, a hard disk, a Random Access Memory (RAM), a Read-Only Memory (ROM), an Erasable Programmable Read-Only Memory (EPROM or a flash memory), an optical fiber, a portable Compact Disc Read-Only Memory (CD-ROM), an optical storage means, a magnetic storage means, or any suitable combination of the above.

The foregoing describes basic principles of the present application with reference to specific embodiments. However, it may be noted that the merits, advantages, effects, and the like mentioned in the present application are merely examples but not limitations, and cannot be considered that these merits, advantages, effects, and the like are essential to the embodiments of the present application. In addition, the specific details disclosed above are intended only for the purpose of illustration and convenience of understanding, and are not limited thereto, and are not intended to limit the present application to the specific details described above.

The block diagrams of components, apparatuses, devices and systems in the present application are merely illustrative examples and are not intended to require or imply that connections, arrangements and configurations must be performed in the manner shown in the block diagrams. As will be recognized by those skilled in the art, these components, apparatuses, devices and systems can be connected, arranged and configured in any manner. Terms such as "comprise", "include", "have" are open words, meaning "include but not limited to", and they can be used interchangeably. Terms "or" and "and" used herein refer to "and/or", and they can be used interchangeably unless the context expressly indicates otherwise. Term "such as" used herein refers to "such as but not limited to" and they can be used interchangeably.

It may also be noted that, in the apparatuses, devices and methods of the present application, components or steps can be decomposed and/or recombined. These decompositions and/or recombination shall be considered as equivalent solutions of the present application.

The foregoing descriptions of the disclosed aspects are provided to enable any person skilled in the art to make or use the present application. Modifications to these aspects are very obvious to those skilled in the art and the general principles defined herein can be applied to other aspects without departing from the scope of the present application. Therefore, the present application is not intended to be limited to the aspects shown herein, but to the widest extent consistent with the principles and novel features disclosed herein.

The above description has been given for the purposes of illustration and description. In addition, the description is not intended to limit the embodiments of the present application to the form disclosed herein. Although a quantity of exemplary aspects and embodiments have been discussed above, those skilled in the art will recognize some variations, modifications, changes, additions, and sub-combinations thereof.

The above are only the implementation manners of the present application, and the description is relatively specific and detailed, but it should not be understood as a limitation to the scope of the present application. It should be pointed out that for those of ordinary skill in the art, without departing from the concept of the present application, several modifications and improvements may be made, and these all fall within the protection scope of this application.

What is claimed is:

1. A super-resolution flow field reconstruction method, comprising:
   superimposing a plurality of frames of contrast-enhanced ultrasound images that are in one time interval and each of which comprises images of a plurality of microbubbles, to obtain a superimposed image comprising a plurality of microbubble trajectories of the plurality of microbubbles;
   performing straight line fitting on the plurality of microbubble trajectories, to obtain a plurality of microbubble trajectory straight lines of the plurality of microbubbles, respectively;
   determining, based on directions and lengths of the plurality of microbubble trajectory straight lines of the plurality of microbubbles and a quantity of superimposed frames and a frame rate of the plurality of frames of contrast-enhanced ultrasound images, directions and velocities of instantaneous movements of the plurality of microbubbles in the time interval; and
   reconstructing a super-resolution flow field based on directions and velocities of instantaneous movements of the plurality of microbubbles in each of different time intervals; wherein
   the superimposing a plurality of frames of contrast-enhanced ultrasound images that are in one time interval and each of which comprises images of a plurality of microbubbles, to obtain a superimposed image comprising a plurality of microbubble trajectories of the plurality of microbubbles comprises:
   performing registration on the plurality of frames of contrast-enhanced ultrasound images that are in the one time interval and each of which comprises the images of the plurality of microbubbles, to obtain a plurality of frames of registered contrast-enhanced ultrasound images each comprising the images of the plurality of microbubbles; and superimposing the plurality of frames of registered contrast-enhanced ultrasound images that are in the one time interval and each of which comprises the images of the plurality of microbubbles, to obtain the superimposed image comprising the plurality of microbubble trajectories of the plurality of microbubbles.

2. The super-resolution flow field reconstruction method according to claim 1, wherein the performing registration on the plurality of frames of contrast-enhanced ultrasound images that are in the one time interval and each of which comprises the images of the plurality of microbubbles, to obtain a plurality of frames of registered contrast-enhanced ultrasound images each comprising the images of the plurality of microbubbles comprises:

performing, by using a multi-scale registration method, registration on the plurality of frames of contrast-enhanced ultrasound images that are in the one time interval and each of which comprises the images of the plurality of microbubbles, to obtain the plurality of frames of registered contrast-enhanced ultrasound images each comprising the images of the plurality of microbubbles.

3. The super-resolution flow field reconstruction method according to claim 2, wherein the multi-scale registration method comprises global decomposition, local decomposition, and detail decomposition according to decomposition scale.

4. The super-resolution flow field reconstruction method according to claim 1, wherein the superimposing a plurality of frames of contrast-enhanced ultrasound images that are in one time interval and each of which comprises images of a plurality of microbubbles, to obtain a superimposed image comprising a plurality of microbubble trajectories of the plurality of microbubbles comprises:

superimposing a plurality of consecutive frames of contrast-enhanced ultrasound images that are in the one time interval and each of which comprises the images of the plurality of microbubbles, to obtain the superimposed image comprising the plurality of microbubble trajectories of the plurality of microbubbles.

5. The super-resolution flow field reconstruction method according to claim 2, wherein the superimposing a plurality of consecutive frames of contrast-enhanced ultrasound images that are in the one time interval and each of which comprises the images of the plurality of microbubbles, to obtain the superimposed image comprising the plurality of microbubble trajectories of the plurality of microbubbles comprises:

superimposing two, three, or four consecutive frames of contrast-enhanced ultrasound images that are in the one time interval and each of which comprises the images of the plurality of microbubbles, to obtain the superimposed image comprising the plurality of microbubble trajectories of the plurality of microbubbles.

6. The super-resolution flow field reconstruction method according to claim 1, wherein the different time intervals comprise:

different time intervals that comprise a same quantity of frames and whose start frames have a same interval.

7. The super-resolution flow field reconstruction method according to claim 1, wherein the superimposing a plurality of frames of contrast-enhanced ultrasound images that are in one time interval and each of which comprises images of a plurality of microbubbles, to obtain a superimposed image comprising a plurality of microbubble trajectories of the plurality of microbubbles comprises:

superimposing the plurality of frames of contrast-enhanced ultrasound images that are in the one time interval and each of which comprises the images of the plurality of microbubbles, to obtain a superimposed image comprising a plurality of preliminary microbubble trajectories of the plurality of microbubbles; and separately performing skeleton extraction on the plurality of preliminary microbubble trajectories in the superimposed image of the plurality of preliminary microbubble trajectories of the plurality of microbubbles, to obtain the plurality of microbubble trajectories.

8. The super-resolution flow field reconstruction method according to claim 7, wherein the separately performing skeleton extraction on the plurality of preliminary microbubble trajectories in the superimposed image of the plurality of preliminary microbubble trajectories of the plurality of microbubbles comprises:

separately performing, by using an iterative erosion algorithm, the skeleton extraction on the plurality of preliminary microbubble trajectories in the superimposed image.

9. The super-resolution flow field reconstruction method according to claim 7, wherein the separately performing skeleton extraction on the plurality of preliminary microbubble trajectories in the superimposed image of the plurality of preliminary microbubble trajectories of the plurality of microbubbles comprises:

separately performing, by using a circumscribed rectangle-maximum grayscale integral axis extraction algorithm, the skeleton extraction on the plurality of preliminary microbubble trajectories in the superimposed image.

10. The super-resolution flow field reconstruction method according to claim 1, wherein the determining, based on directions and lengths of the plurality of microbubble trajectory straight lines of the plurality of microbubbles and a quantity of superimposed frames and a frame rate of the plurality of frames of contrast-enhanced ultrasound images, directions and velocities of instantaneous movements of the plurality of microbubbles in the time interval comprises:

determining, based on the directions of the plurality of microbubble trajectory straight lines of the plurality of microbubbles, the directions of instantaneous movements of the plurality of microbubbles in the time interval; and determining, based on a product of the frame rate and a ratio of the lengths of the microbubble trajectory straight lines of the plurality of microbubbles to the quantity of superimposed frames of the plurality of frames of contrast-enhanced ultrasound images, the velocities of instantaneous movements of the plurality of microbubbles in the time interval.

11. The super-resolution flow field reconstruction method according to claim 1, wherein each microbubble trajectory straight line of each microbubble in the plurality of microbubble trajectory straight lines of the plurality of microbubbles comprises at least one pixel coordinate; and the reconstructing a super-resolution flow field based on directions and velocities of instantaneous movements of the plurality of microbubbles in each of different time intervals comprises:
determining, based on the directions and velocities of instantaneous movements of the plurality of microbubbles in each of the different time intervals, directions and velocities of instantaneous movements of the plurality of microbubbles, in each of the different time intervals, corresponding to a plurality of pixel coordinates; and
reconstructing the super-resolution flow field based on the directions and velocities of instantaneous movements of the plurality of microbubbles, in each of the different time intervals, corresponding to the plurality of pixel coordinates.

12. The super-resolution flow field reconstruction method according to claim 11, wherein a plurality of microbubble trajectories of the each microbubble comprise same pixel coordinates; and
the reconstructing the super-resolution flow field comprises:
calculating a frequency of occurrence of each of directions and velocities of instantaneous movements corresponding to the same pixel coordinates of the each microbubble, and selecting a direction and a velocity, having the highest frequency of occurrence, of instantaneous movements to reconstruct the super-resolution flow field.

13. The super-resolution flow field reconstruction method according to claim 11, wherein a plurality of microbubble trajectories of the each microbubble comprise same pixel coordinates; and
the reconstructing the super-resolution flow field comprises:
calculating an average value of each of directions and velocities of instantaneous movements corresponding to the same pixel coordinates of the each microbubble, to reconstruct the super-resolution flow field.

14. The super-resolution flow field reconstruction method according to claim 11, wherein a plurality of microbubble trajectories of the each microbubble comprise same pixel coordinates; and
the reconstructing the super-resolution flow field comprises:
calculating a maximum value of each of directions and velocities of instantaneous movements corresponding to the same pixel coordinates of the each microbubble to reconstruct the super-resolution flow field.

15. The super-resolution flow field reconstruction method according to claim 1, wherein the performing straight line fitting on the plurality of microbubble trajectories, to obtain a plurality of microbubble trajectory straight lines of the plurality of microbubbles, respectively comprises:
performing, by using a Hough transform-based straight line detection method, straight line fitting on the plurality of microbubble trajectories, to obtain the plurality of microbubble trajectory straight lines of the plurality of microbubbles, respectively.

16. An electronic device, comprising:
a processor; and
a memory, wherein the memory stores computer program instructions, and when the computer program instructions are run by the processor, the processor is enabled to perform the super-resolution flow field reconstruction method according to claim 1.

17. The electronic device according to claim 16, wherein the superimposing a plurality of frames of contrast-enhanced ultrasound images that are in one time interval and each of which comprises images of a plurality of microbubbles, to obtain a superimposed image comprising a plurality of microbubble trajectories of the plurality of microbubbles comprises:
superimposing a plurality of consecutive frames of contrast-enhanced ultrasound images that are in the one time interval and each of which comprises the images of the plurality of microbubbles, to obtain the superimposed image comprising the plurality of microbubble trajectories of the plurality of microbubbles.

18. A non-transitory computer-readable storage medium storing computer program instructions for executing the super-resolution flow field reconstruction method according to claim 1.

* * * * *